US009059547B2

(12) United States Patent
McLawhorn

(10) Patent No.: US 9,059,547 B2
(45) Date of Patent: Jun. 16, 2015

(54) LEAD SYSTEM FOR ELECTRICAL DEVICES USED IN MEDICAL PROCEDURES

(75) Inventor: Tyler E. McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1005 days.

(21) Appl. No.: 13/112,358

(22) Filed: May 20, 2011

(65) Prior Publication Data

US 2012/0130365 A1 May 24, 2012

Related U.S. Application Data

(60) Provisional application No. 61/346,735, filed on May 20, 2010.

(51) Int. Cl.
| | |
|---|---|
| *H01R 13/62* | (2006.01) |
| *H01R 24/28* | (2011.01) |
| *A61B 18/14* | (2006.01) |
| *H01R 27/00* | (2006.01) |
| *A61B 18/00* | (2006.01) |
| *H01R 103/00* | (2006.01) |

(52) U.S. Cl.
CPC .............. *H01R 24/28* (2013.01); *A61B 18/14* (2013.01); *A61B 2018/00178* (2013.01); *H01R 27/00* (2013.01); *H01R 2103/00* (2013.01); *H01R 2201/12* (2013.01)

(58) Field of Classification Search
CPC ................................. H01R 13/05; H01R 13/46
USPC ........................ 439/296, 346, 347, 304, 131
See application file for complete search history.

(56) References Cited

U.S. PATENT DOCUMENTS

| | | | |
|---|---|---|---|
| 1,503,011 | A | 3/1925 | Pacent |
| 2,151,226 | A | 3/1939 | Ogle |
| 2,210,418 | A | 8/1940 | Larson |
| 2,496,173 | A | 1/1950 | Peebles |
| 3,204,213 | A | 8/1965 | Bauer |
| 3,603,860 | A | 9/1971 | Johnson |
| 4,013,334 | A | 3/1977 | Behnke |
| 4,754,256 | A | 6/1988 | Fluhr et al. |
| 4,886,469 | A | 12/1989 | Jseng |
| 5,106,317 | A | 4/1992 | Taylor |
| 5,176,136 | A | 1/1993 | Giele |

(Continued)

FOREIGN PATENT DOCUMENTS

| | | |
|---|---|---|
| DE | 15 90 834 A1 | 6/1970 |
| EP | 0 033 723 A2 | 8/1981 |

(Continued)

OTHER PUBLICATIONS

JP Office Action for corresponding Japanese Application No. 2013-511375 with English Language Translation, dated Feb. 12, 2014, 4 p.

(Continued)

*Primary Examiner* — Phuongchi T Nguyen
(74) *Attorney, Agent, or Firm* — Brinks Gilson & Lione

(57) ABSTRACT

A lead system for electrical devices is disclosed that includes a first lead and a second lead, where the second lead may be in communication with a sliding member and a lead channel. The second lead translates laterally along the lead channel between a plurality of positions so as to vary the spacing between the first lead and the second lead.

16 Claims, 7 Drawing Sheets

(56) References Cited

U.S. PATENT DOCUMENTS

| | | | |
|---|---|---|---|
| 5,295,845 | A | 3/1994 | Changxing |
| 5,683,385 | A | 11/1997 | Kortenbach et al. |
| 5,716,219 | A | 2/1998 | Noike |
| 6,113,596 | A | 9/2000 | Hooven et al. |
| 6,126,462 | A | 10/2000 | Lam |
| 6,585,530 | B2 | 7/2003 | Steiert et al. |
| 6,780,034 | B2 | 8/2004 | Shiroshita et al. |
| 6,923,666 | B1 | 8/2005 | Liao |
| 6,939,150 | B1 | 9/2005 | Lanni |
| 7,052,298 | B1 | 5/2006 | Cheng |
| 7,059,878 | B1 | 6/2006 | Hendrixson |
| 7,204,703 | B1 | 4/2007 | Hendrixson |
| 7,306,471 | B2 | 12/2007 | Shau-din |
| 7,488,215 | B2 | 2/2009 | Mayette et al. |
| 2002/0116035 | A1 | 8/2002 | Klehn |
| 2006/0079871 | A1 | 4/2006 | Plaven et al. |
| 2009/0284221 | A1 | 11/2009 | Liao |
| 2010/0068949 | A1 | 3/2010 | Plaven et al. |

FOREIGN PATENT DOCUMENTS

| | | |
|---|---|---|
| EP | 0 502 685 A2 | 9/1992 |
| EP | 1 647 234 A1 | 4/2006 |
| GB | 607 850 | 9/1948 |
| GB | 2210211 | 6/1989 |
| JP | 1989-121274 | 8/1989 |
| JP | 1993-65072 | 8/1993 |
| JP | 2003-132991 | 5/2003 |
| WO | WO 2009/024777 A1 | 2/2009 |

OTHER PUBLICATIONS

Patent Examination Report dated Apr. 26, 2013, 5 p., for corresponding Australian Patent Application No. 2011255444, filed on May 20, 2011.

Annex to Form PCT/ISA/206 *Communication Relating to the Results of the Partial International Search* issued in corresponding PCT/US2011/037294 on Jul. 29, 2011 (3 pgs).

CEI/IEC 60601-2-2:2006; Fourth Edition 2006-2007; Medical Electrical Equipment (174 pgs).

LEAD SYSTEM FOR ELECTRICAL DEVICES USED IN MEDICAL PROCEDURES

This application claims priority to U.S. Provisional Application Ser. No. 61/346,735, filed May 20, 2010.

BACKGROUND

The present system relates to electrical devices, and more particularly, to leads for use in medical procedures.

Electrosurgical techniques are used in both open and minimally invasive surgical procedures. In such techniques, high frequency electric current is applied to biological tissue as a means to cut, coagulate, desiccate, or fulgurate tissue. Electrosurgical techniques are beneficial because the techniques include the ability to make precise cuts with limited blood loss. More specifically, electrosurgery employs 0.5-2 MHz (alternating) radiofrequency current applied to a small area (active) electrode.

Generally, electrosurgical instruments are of two types: monopolar and bipolar. A monopolar electrosurgical system includes an instrument comprising an electrode that is conductively connected to the active terminal of a monopolar RF generator. Monopolar electrosurgical instruments are used primarily for electrosurgical cutting of tissue and provide for generally wide-reaching coagulation. Bipolar electrosurgical systems, on the other hand, include instruments which have both positive and negative electrodes on the instrument itself, which electrodes are connected to the positive and negative terminals of a bipolar RF generator. Bipolar electrosurgical instruments generally provide the physician with greater control of the path of the RF energy through the patient, as the RF energy generally passes only though the tissue located between the electrodes of opposite polarity on the instrument, and not otherwise through the patient's body. Thus, bipolar electrosurgical instruments may provide for a more refined surgical technique and more predictable current flow.

Bipolar electrosurgical instruments, e.g., endoscopic accessories, must have the ability to connect to a standard electrosurgical unit (ESU). Depending on the specific unit, this connection can be a mono plug or a dual plug. See, for example, BCP-7A (dual plug) and BCP-7B (mono plug) Quicksilver Bipolar® Probes (supplied by Cook Medical, Bloomington, Ind. 47402). The connection points for a dual plug on ESUs are a fixed distance from one another.

Because of the nature of dual plugs, too much slack between the leads leaves the opportunity for the end user to incorrectly connect the bipolar device to the ESU or other nearby unit, thus posing a risk to user or patient, or causing device malfunction. To avoid this type of misconnection, the leads on the bipolar device can simply be fixed a set distance from one another to adequately mate to the fixed distance connection point on the ESU. More particularly, safety requirements for the use of high frequency surgical equipment dictate that active connectors having more than one pin shall have fixed pin spacing, and that "flying" leads are prohibited. Fixed is defined in these requirements as meaning fastened or otherwise secured at a specific location either permanently or so that it can only be detached by means of a tool, i.e., making removal or opening difficult without using a tool.

However, different ESUs have different set distances of connection points, thus requiring different lead devices depending on the distance of the connection points on a particular ESU. A need therefore exists for devices that provide variable fixed leads so as to be compatible with ESUs that may have varying lead distances.

BRIEF SUMMARY

The foregoing problems are solved and technical advance is achieved with an illustrative lead system for electrical devices used in medical procedures. The lead system may include a housing, a fixed lead secured to the housing and a variable lead connected to the housing. The lead system also may include a mechanism for translating the position of the variable lead relative to the housing so as to vary the spacing between the fixed lead and variable lead. The lead system also may include a locking mechanism for locking the variable lead against movement relative to the housing. The system has the advantage of being able to provide variable fixed leads for compatibility with varied electrical devices.

These and other advantages, as well as the lead system itself, will become apparent in the details of construction and operation as more fully described below. Moreover, it should be appreciated that several aspects of the invention can be used with other types of electrical and medical devices.

DETAILED DESCRIPTION OF THE DRAWINGS AND THE PRESENTLY PREFERRED EMBODIMENTS

For the purposes of promoting an understanding of the principles of the lead system for electrical devices, reference will now be made to the embodiments illustrated herein. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

Figure 1:
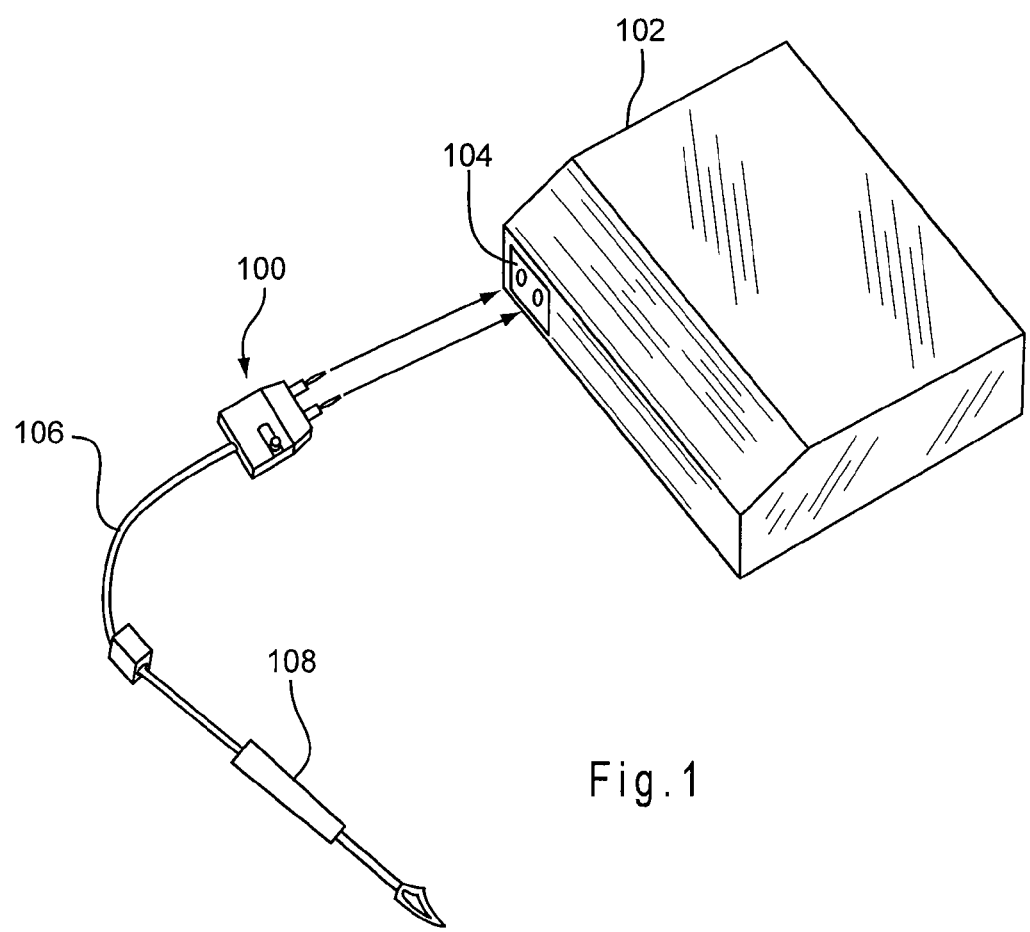
FIG. 1 is an illustration of the lead system for electrical devices used in medical procedures illustrating one embodiment of the lead system.

Referring now to FIG. 1, a lead system 100 is shown for use in conjunction with an electrosurgical device 102. It should be understood at the outset that the lead system 100 illustrated in FIG. 1 may employ any of the embodiments described herein, as well as others, and that it is the following claims, including all equivalents, that are intended to define the spirit and scope of this invention. For example, the lead system 100 may include other components that guide movement of various components of the system that are not shown in the Figures but nonetheless aid the operation of the lead system 100. Likewise, though an electrosurgical device 102 is shown by way of example only, use of the lead system 100 in other clinical situations is envisioned. Further, while certain features of the electrosurgical device 102 are shown, it should be understood that the electrosurgical device 102 is a standard electrosurgical device, and various components are shown for illustration purposes only.

The electrosurgical device 102 includes an input receptacle 104 that can be mono-plug or dual-plug. The input receptacle 104 may receive the lead system 100 when the lead system 100 is plugged in to the input receptacle 104 of the electrosurgical device 102. Removably attached to the lead system 100 is an instrument cable 106 that is connected with an instrument 108. The instrument 108 may be any instrument for use in the clinical environment that would benefit from the advantages disclosed herein. For example, the instrument 108 could be scissors, graspers, forceps, or any other instrument having electrodes associated therewith.

Figure 2:
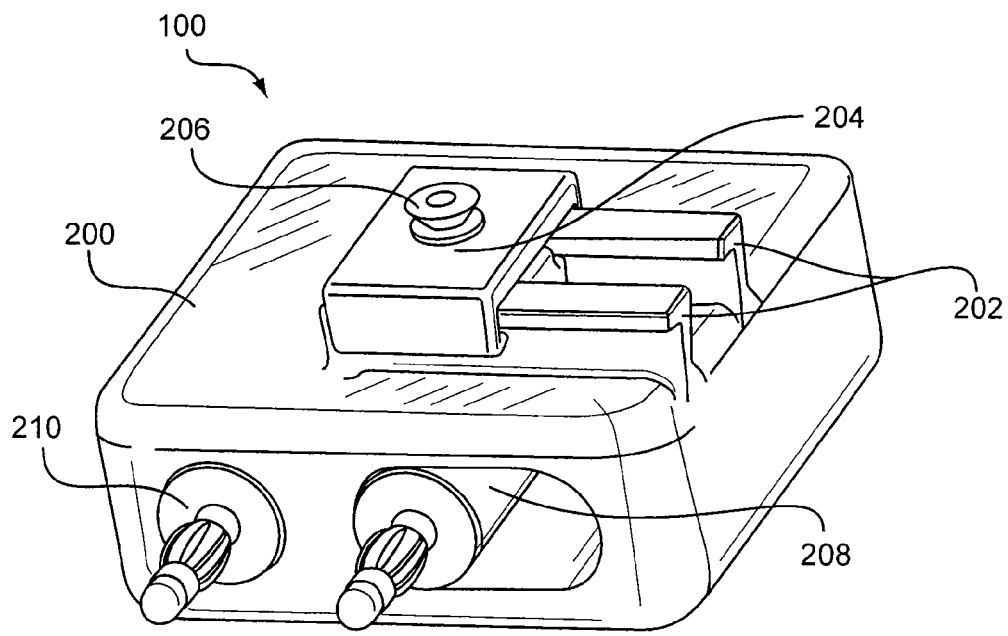
FIG. 2 is an illustration of the lead system illustrating a variable lead positioned in a first position along the housing.
Figure 3:
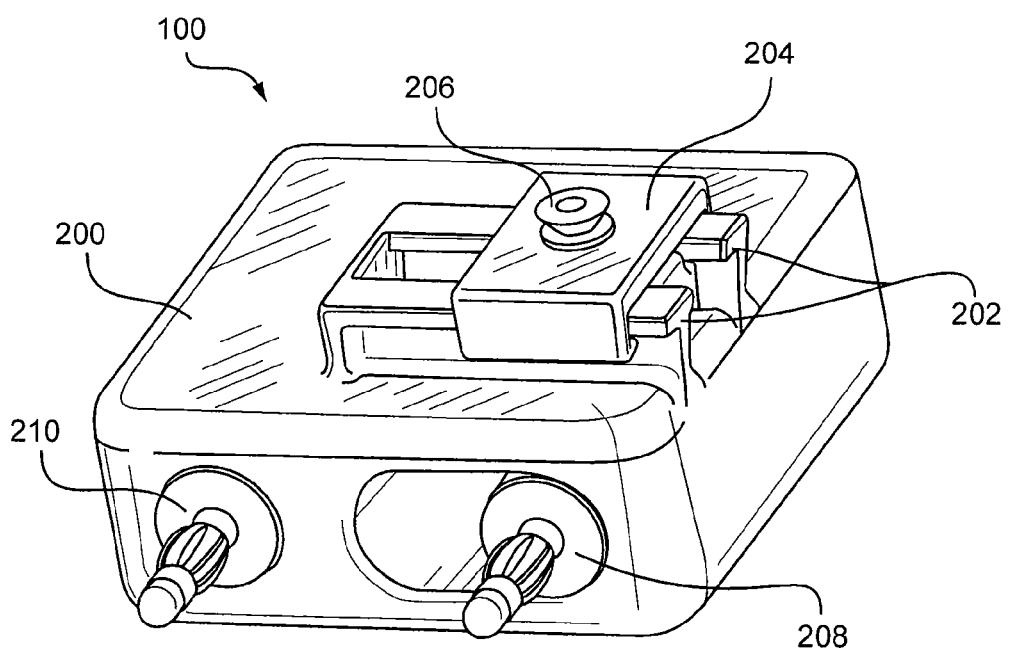
FIG. 3 is an illustration of the variable lead system illustrating a variable lead positioned in a second position along the housing.

FIGS. 2-12 illustrate various embodiments of the lead system 100. FIGS. 2 and 3 illustrate the lead system 100 having a housing 200. The housing 200 may be various shapes, such as illustrated herein or designed more aesthetically or functionally as the application requires. Formed on the top of the housing 200 are housing tracks 202, upon which a sliding member 204 is slidably attached and may translate. Although two housing tracks 202 are shown, it should be understood that one track could be implemented, as well as more than two tracks, depending on the application of the lead system 100. The sliding member 204 may also be in communication with a locking mechanism 206. The locking mechanism 206 may be a hex screw or some other mechanism to stop the sliding member 204 from freely translating along the housing tracks 202. To allow translation of the sliding member 204, a user may simply unlock or loosen the locking mechanism 206 and maneuver the sliding member 204. To illustrate this ability, FIG. 2 illustrates the sliding member 204 in a first position in relation to the housing 200 and FIG. 3 illustrates the sliding member 204 in a second position in relation to the housing 200.

Also shown in FIGS. 2 and 3 is variable lead 208. Variable lead 208 is in communication with the sliding member 204 (as further explained below) such that when the sliding member 204 translates along the housing tracks 202, the variable lead 208 translates in a similar direction. A fixed lead 210 is also shown. The variable lead 208 is laterally moveable between a plurality of positions so as to vary the spacing between the fixed lead 210 and the variable lead 208. There also may be detents (not shown) included or other markings or indicia included on the lead system 100, for example, on the housing tracks 202 or elsewhere on the housing 200. The detents may be distributed along the tracks 202 or housing 200 at predetermined locations along which the variable lead 208 may translate. While a fixed lead 210 is shown, it should be understood that an additional variable lead could be included in the manner described above, and further described below in relation to FIG. 11.

Figure 4:
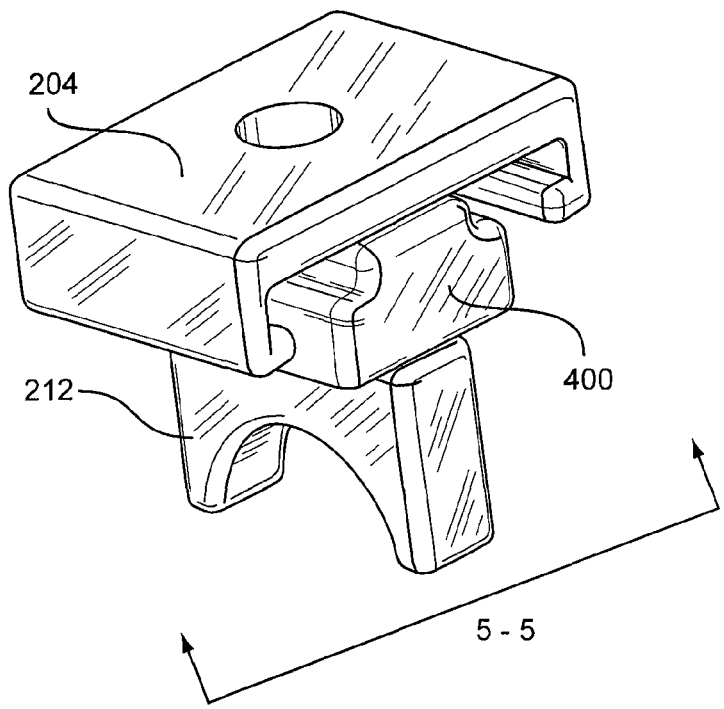
FIG. 4 is an illustration of aspects of the lead system shown in FIG. 2.
Figure 5:
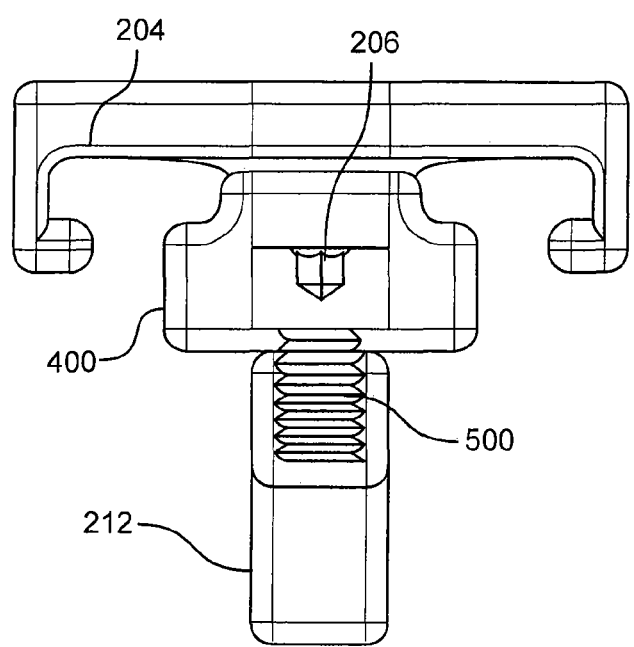
FIG. 5 is an illustration taken along line 5-5 of FIG. 4.

FIGS. 4 and 5 illustrate how the variable lead 208 translates with the sliding member 204. Shown in FIG. 4 is the sliding member 204 engaging a lead channel 212 and a channel component 400. The channel component 400 translates within the housing track 202 and engages the lead channel 212. The lead channel 212 aids the translation of the variable lead 208 (not shown) by engaging the variable lead 208. FIG. 5 illustrates how this translation occurs, and is taken along line 5-5 in FIG. 4. The locking mechanism 206 is shown extending securely into the portion of the channel component 400 illustrated in FIG. 5. As the locking mechanism 206 is tightened, the sliding member 204 is secured against the housing tracks 202, thus impeding translation of the sliding member along the housing tracks 202. As the locking mechanism 206 is loosened, released or removed from the housing 200, it no longer impedes movement of the sliding member 204, and the sliding member 204 can translate freely along the housing tracks 202. As shown in FIG. 5, a channel post 500 is attached to the channel component 400 and is engaged with the lead channel 212. The sliding member 204 is laterally moveable between a plurality of positions so as to vary the spacing between the fixed lead 210 and the variable lead 208.

Figure 6:
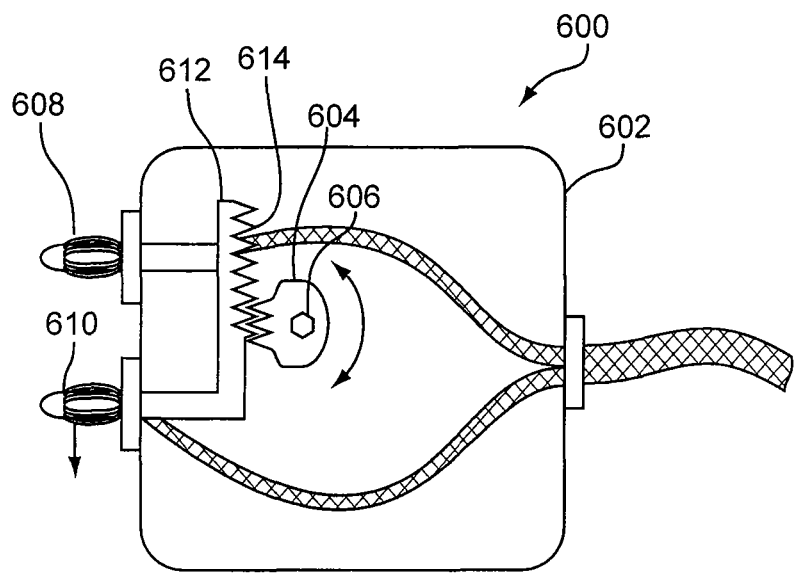
FIG. 6 is an alternative embodiment of the lead system for electrical devices used in medical procedures.
Figure 7:
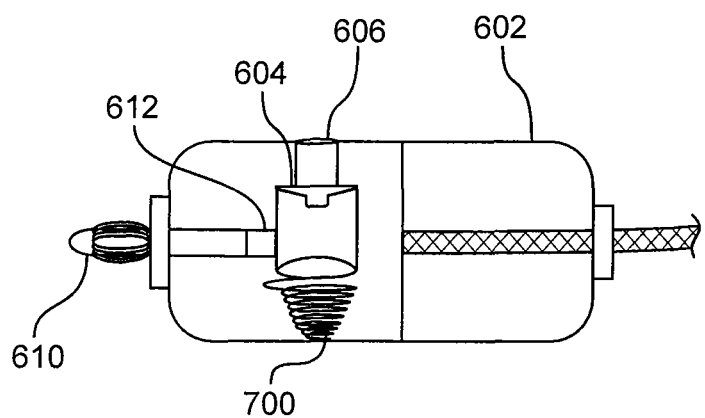
FIG. 7 is a side view of the embodiment illustrated in FIG. 6.

FIGS. 6 and 7 illustrate an alternative embodiment of the lead system illustrated in FIGS. 2-5. In FIG. 6, a lead system 600 is shown, including a housing 602. The housing 602 may be various shapes, such as illustrated herein or designed more aesthetically or functionally as the application requires. The lead system 600 may also include a gear 604 and a tool 606. The tool 606 preferably is a hex screw or some other mechanism that, upon rotation, mechanically rotates the gear 604. The gear 604 engages a gear bar 612, which is in communication with the variable lead 610. The gear bar 612 has gear teeth 614 that are in communication with the gear 604. While a certain number of gear teeth 614 are shown, it should be understood that the number of gear teeth 614 can vary, depending on the particular application. The tool 606 may also be pushed down to lock (or fix) the variable lead 610 as further described below in reference to FIG. 7. The tool 606 may be used to secure or release or to make adjustments. A fixed lead 608 may also be included. The fixed lead 608 is fastened or otherwise secured at a specific location either permanently or so that it may only be removed by means of an implement.

FIG. 7 illustrates a side view of the embodiment shown in FIG. 6. FIG. 7 includes a locking mechanism 700, which locks or fixes the variable lead 610 when the tool 606 is pressed down toward the locking mechanism 700.

Figure 8:
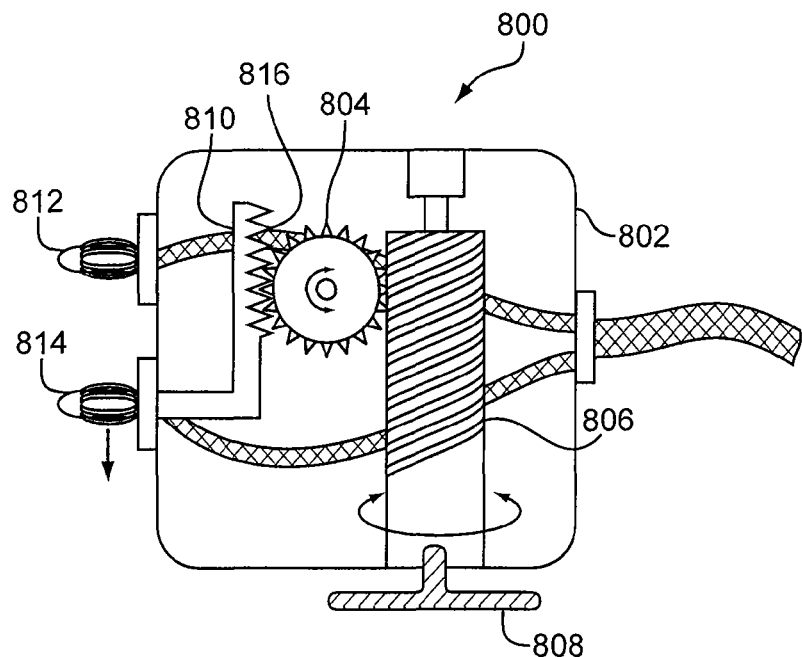
FIG. 8 is an alternative embodiment of the lead system for electrical devices used in medical procedures.

FIG. 8 illustrates another alternative embodiment of the lead system. In FIG. 8, a lead system 800 is shown, including a housing 802. The housing 802 may be various shapes, such as illustrated herein or designed more aesthetically or functionally as the application requires. A fixed lead 812 may also be included. The lead system 800 includes a gear 804 and a tool 806. The tool 806 preferably is a hex screw or some other mechanism that, upon rotation, mechanically rotates the gear 804, which in turn interacts with a gear bar 810 attached to a variable lead 814 so as to vary the spacing between the variable lead 814 and the fixed lead 812. The gear bar 810 has gear teeth 816 that are in communication with the gear 804. While a certain number of gear teeth 816 are shown, it should be understood that the number of gear teeth 816 can vary, depending on the particular application. The tool 806 may also include a knob 808 extending outside the housing 802 which enables a user to rotate the tool 806.

Once the variable lead 814 is set at the appropriate distance (i.e., the distance necessary for a particular application) from the fixed lead 812, the variable lead 814 is fastened or otherwise secured at a specific location so that it can only be detached by means of an implement, such as fastening means (screws, nuts, etc.), making removal/opening difficult without using an implement. The knob 808 may be removable so as to prevent the rotation of the tool 806.

Figure 9:
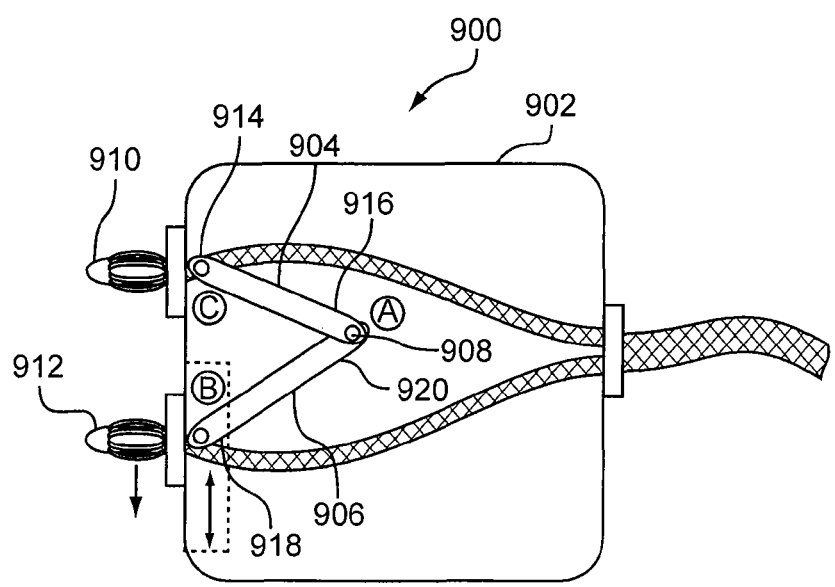
FIG. 9 is an alternative embodiment of the lead system for electrical devices used in medical procedures.

FIG. 9 illustrates another alternative embodiment of the lead system. In FIG. 9, a lead system 900 is shown, including a housing 902. The housing 902 may be various shapes, such as illustrated herein or designed more aesthetically or functionally as the application requires. The lead system 900 includes a first bar 904 having a first end 914 and a second end 916 and a second bar 906 having a first end 918 and a second end 920, the first bar 904 and the second bar 906. The second end 916 of the first bar 904 and the second end 920 of the second bar 906 are linked together by a linking mechanism 908. The linking mechanism 908 may be a pin, screw, or other means that links the two bars 904 and 906 together. A fixed lead 910 and a variable lead 912 may also be included. The fixed lead 910 is fastened or otherwise secured at a specific location either permanently or so that it can only be detached by means of a tool, such as fastening means (screws, nuts, etc.), making removal/opening difficult without using a tool. The variable lead 912 may translate towards and away from the fixed lead 910 (along a vertical pathway in FIG. 9) by movement at the linkage point of the linking mechanism 908 (along a horizontal pathway in FIG. 9). For example, the housing 902 may comprise a horizontal slot (not shown) along which the linking mechanism 908 may translate and be secured thereto. Once the variable lead 912 is set at the appropriate distance from the fixed lead 910 (i.e., the distance necessary for a particular application), the variable lead 912 is fastened or otherwise secured by fixing the position of the linking mechanism 908 at a specific location relative to the housing 902.

Figure 10:
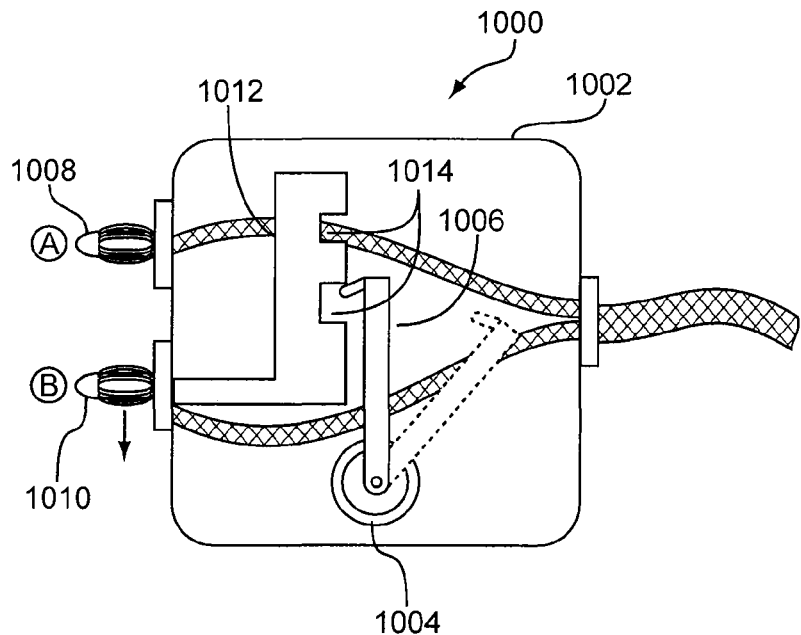
FIG. 10 is an alternative embodiment of the lead system for electrical devices used in medical procedures.

FIG. 10 illustrates another alternative embodiment of the lead system. In FIG. 10, a lead system 1000 is shown, including a housing 1002. The housing 1002 may be various shapes, such as illustrated herein or designed more aesthetically or functionally as the application requires. The lead system 1000 includes a torsion spring 1004 and a pivotal lever 1006, along with a fixed lead 1008, a variable lead 1010, and a lead bar 1012. The torsion spring 1004 is operably connected to the lever 1006 and biases the lever 1006 towards and into engagement with the lead bar 1012. For example, if the torsion spring 1004 is rotated in a clockwise manner, the lever 1006 disengages from the lead bar 1012, thereby allowing a user to translate the variable lead 1010 into a different position. When the user releases the lever 1006, the torsion spring 1004 then rotates the lever counterclockwise to reengage the lead bar 1012 and lock the variable lead 1010 in place. The lead bar 1012 includes a plurality of receptacles 1014 in which the lever 1006 may rest. While only a pair of receptacles 1014 are shown, it should be understood that the lead bar 1012 can have any number of receptacles 101, and any spacing, depending on the number of positions desired for the variable lead 1010.

Figure 11:
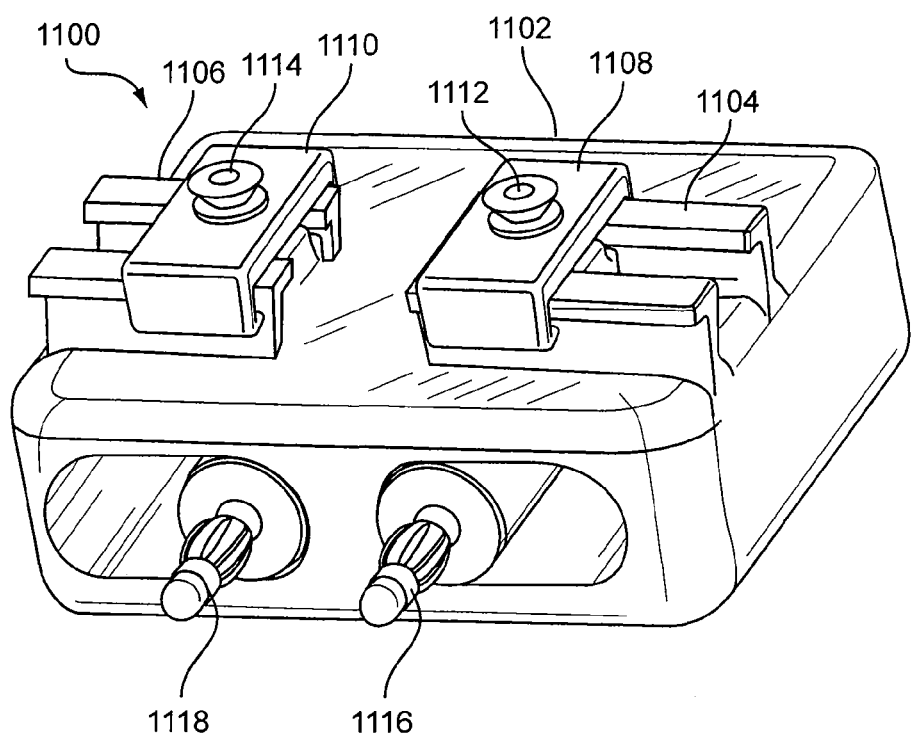
FIG. 11 is an alternative embodiment of the lead system for electrical devices used in medical procedures.

FIG. 11 illustrates another alternative embodiment of the lead system. The lead system illustrated in FIG. 11 is similar to the lead system illustrated in FIGS. 2-5, but comprises a pair of variable leads (as opposed to only a single variable lead). The lead system 1100 is shown having a housing 1102. The housing 1102 may be various shapes, such as illustrated herein or designed more aesthetically or functionally as the application requires. Formed on the top of the housing 1102 are a first set of housing tracks 1104 and a second set of housing tracks 1106. A first sliding member 1108 is shown engaging the first set of housing tracks 1104, and a second sliding member 1110 is shown engaging the second set of housing tracks 1106. The sliding members 1108 and 1110 may translate along each respective set of housing tracks 1104 and 1106. The first sliding member 1108 may also be in communication with a first locking mechanism 1112. The locking mechanism 1112 may be a hex screw or some other mechanism to stop the first sliding member 1108 from freely translating along the housing tracks 1104. To allow translation of the sliding member 1108, a user may simply unlock the locking mechanism 1112 and maneuver the sliding member 1108 from, for example, a first position to a second position. In similar manner, the second sliding member 1110 may also be in communication with a second locking mechanism 1114. The locking mechanism 1114 may be a hex screw or some other mechanism to stop the second sliding member 1110 from freely translating along the housing tracks 1106. To allow translation of the sliding member 1110, a user may simply unlock the locking mechanism 1114 and maneuver the sliding member 1110 from, for example, a first position to a second position.

Also shown in FIG. 11 is a first lead 1116 and a second lead 1118. The first lead 1116 is in communication with the first sliding member 1108 such that when the first sliding member 1108 translates along the first set of housing tracks 1104, the first lead 1116 translates in a similar. The second lead 1118 is in communication with the second sliding member 1110 such that when the second sliding member 1110 translates along the second set of housing tracks 1106, the second lead 1118 translates in a similar direction. The first lead 1116 and second lead 1118 are laterally moveable between a plurality of positions so as to vary the spacing between the first lead 1116 and the second lead 1118.

Figure 12:
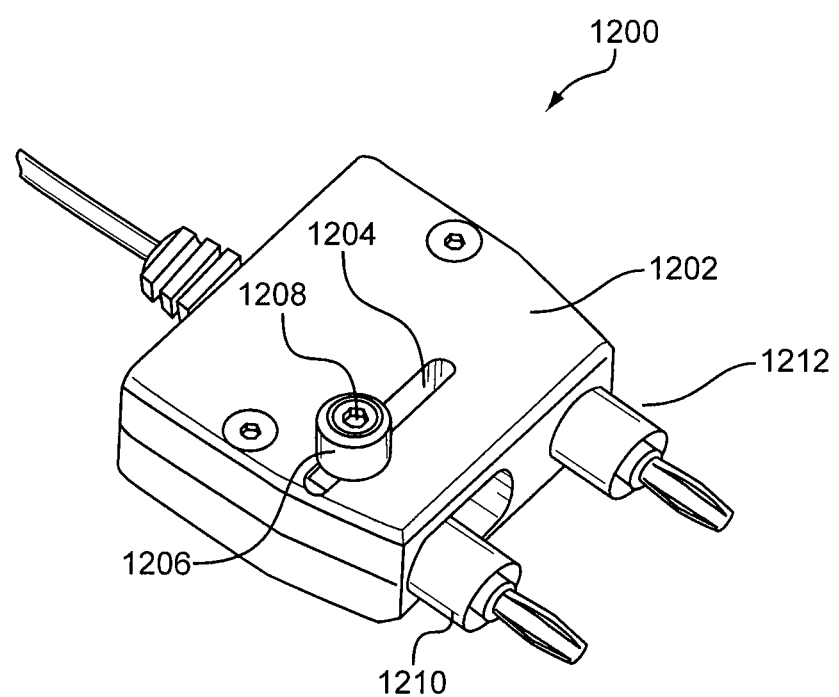
FIG. 12 is an alternative embodiment of the lead system for electrical devices used in medical procedures.

FIG. 12 illustrates another alternative embodiment of the lead system, which is similar to the lead system illustrated in FIGS. 2-5. In FIG. 12, a lead system 1200 is shown, including a housing 1202. The housing 1202 may be various shapes, such as illustrated herein or designed more aesthetically or functionally as the application requires. The lead system 1200 includes a housing channel 1204 through which a sliding member 1206 may translate. The sliding member 1206 may be in communication with a locking mechanism 1208. The locking mechanism 1208 may be a hex screw or some other mechanism to stop the sliding member 1206 from freely translating within the housing channel 1204. To allow translation of the sliding member 1206, a user simply unlocks or loosens the locking mechanism 1208 to allow the sliding member 1206 to translate along the housing channel 1204.

Also shown in FIG. 12 is a variable lead 1210. The variable lead 1210 is in communication with the sliding member 1206 such that when the sliding member 1206 translates through the housing channel 1204, the variable lead 1210 translates in a similar direction. A fixed lead 1212 is also shown. The variable lead 1210 is laterally moveable between a plurality of positions so as to vary the spacing between the fixed lead 1212 and the variable lead 1210. While a fixed lead 1212 is shown, it should be understood that an additional variable lead could be included in the manner described above. For example, the housing channel 1204 could extend across the housing 1202 thereby providing room for an additional sliding member in communication with an additional variable lead.

It should be understood that the principles disclosed herein may be applied to the input receptacles of an electrosurgical unit, such that the input receptacles are variable instead of fixed and are configured to receive mono-plug or dual-plug leads. It is therefore intended that the foregoing detailed description be regarded as illustrative rather than limiting, and that it be understood that it is the following claims, including all equivalents, that are intended to define the spirit and scope of this invention.

The invention claimed is:

1. A lead system for electrical devices, comprising:
a housing;
a fixed lead fixedly secured to the housing;
a variable lead movably connected to the housing;
a mechanism for translating a position of the variable lead relative to the housing so as to vary a spacing between the fixed lead and variable lead, the mechanism comprising one or more of:
   a) a gear, a gear bar fixedly attached to the variable lead and in communication with the gear, and a tool in communication with the gear;
   b) a first bar, where one end of the first bar is in communication with the fixed lead and another end of the first bar is in communication with a second bar by linking means, where an end of the second bar is in communication with the variable lead;
   c) a lead bar fixedly attached to the variable lead, a lever in communication with the lead bar, and a torsion spring fixedly attached to the lever; and
a locking mechanism for locking the variable lead against movement relative to the housing.

2. The lead system of claim 1, further comprising an electrosurgical unit having a first input receptacle and a second input receptacle configured to receive the fixed lead and the variable lead.

3. The lead system of claim 1, where the mechanism for translating the variable lead along the housing comprises a sliding member in communication with the variable lead and the locking mechanism.

4. The lead system of claim 1 wherein the locking mechanism is operably connected between the mechanism for translating the position of the variable lead relative to the housing and the housing.

5. The lead system of claim 1, where the fixed lead and the variable lead are operably configured to be connected to an electrosurgical unit.

6. The lead system of claim 1, where the lead system is operably configured to be connected to an instrument cable.

7. The lead system of claim 1, further comprising an instrument cable operably connected to the lead system, and an instrument connected to the instrument cable.

8. The lead system of claim 1 where the housing further comprises a housing track and a lead channel formed thereon.

9. The lead system of claim 8 where the mechanism for translating the position of the variable lead relative to the housing is in communication with the lead channel.

10. The lead system of claim 8 where the mechanism for translating the variable lead along the housing comprises a sliding member in communication with the variable lead.

11. The lead system of claim 10 where the sliding member is configured to translate the variable lead along the lead channel between a plurality of positions so as to vary the spacing between the fixed lead and variable lead.

12. A variable lead system for an electrosurgical device, comprising:
a housing with a housing track and a lead channel formed thereon;
a sliding member slidably attached to the housing track, where the sliding member translates along the housing track;
a fixed lead secured at a location on the housing;
a variable lead movably disposed along the lead channel and projecting outwardly from the housing, the variably lead being operably connected to the sliding member, the sliding member being configured to laterally move the variable lead along the lead channel between a plurality of positions so as to vary the spacing between the fixed lead and variable lead;
a mechanism for translating the variable lead along the housing, the mechanism comprising one or more of:
   a) a gear, a gear bar fixedly attached to the variable lead and in communication with the gear, and a tool in communication with the gear;
   b) a first bar, where one end of the first bar is in communication with the fixed lead and another end of the first bar is in communication with a second bar by linking means, where an end of the second bar is in communication with the variable lead;
   c) a lead bar fixedly attached to the variable lead, a lever in communication with the lead bar, and a torsion spring fixedly attached to the lever; and
a locking mechanism for temporarily securing the variable lead in one of the plurality of positions.

13. The lead system of claim 12, further comprising and instrument cable connected to the lead system, and an instrument connected to the instrument cable.

14. A lead system for electrical devices, comprising:
a housing;
a fixed lead fixedly secured to the housing;
a variable lead movably connected to the housing;
a mechanism for translating a position of the variable lead relative to the housing so as to vary a spacing between the fixed lead and variable lead; and
a locking mechanism for locking the variable lead against movement relative to the housing,
wherein the mechanism for translating the variable lead along the housing comprises a gear, a gear bar fixedly attached to the variable lead and in communication with the gear, and a tool in communication with the gear.

15. A lead system for electrical devices, comprising:
a housing;
a fixed lead fixedly secured to the housing;
a variable lead movably connected to the housing;
a mechanism for translating a position of the variable lead relative to the housing so as to vary a spacing between the fixed lead and variable lead; and
a locking mechanism for locking the variable lead against movement relative to the housing,
wherein the mechanism for translating the variable lead along the housing comprises a first bar, where one end of the first bar is in communication with the fixed lead and another end of the first bar is in communication with a second bar by linking means, where an end of the second bar is in communication with the variable lead.

16. A lead system for electrical devices, comprising:
a housing;
a fixed lead fixedly secured to the housing;
a variable lead movably connected to the housing;
a mechanism for translating a position of the variable lead relative to the housing so as to vary a spacing between the fixed lead and variable lead; and
a locking mechanism for locking the variable lead against movement relative to the housing,
wherein the mechanism for translating the variable lead along the housing comprises a lead bar fixedly attached to the variable lead, a lever in communication with the lead bar, and a torsion spring fixedly attached to the lever.

* * * * *